(12) United States Patent
Leitgeb et al.

(10) Patent No.: US 12,372,462 B2
(45) Date of Patent: Jul. 29, 2025

(54) METHOD FOR CONTROLLING A SEMICONDUCTOR-LASER-DIODE-BASED SS-INTERFEROMETER SYSTEM

(71) Applicant: Carl Zeiss Meditec AG, Jena (DE)

(72) Inventors: Rainer Leitgeb, Vienna (AT); Manfred Dick, Gefell (DE); Roland Bergner, Jena (DE); Ralf Ebersbach, Schmölln (DE); Thomas Pabst, Stadtroda (DE)

(73) Assignee: Carl Zeiss Meditec AG, Jena (DE)

( * ) Notice: Subject to any disclaimer, the term of this patent is extended or adjusted under 35 U.S.C. 154(b) by 680 days.

(21) Appl. No.: 17/433,776

(22) PCT Filed: Feb. 28, 2020

(86) PCT No.: PCT/EP2020/055291
§ 371 (c)(1),
(2) Date: Mar. 24, 2022

(87) PCT Pub. No.: WO2020/174088
PCT Pub. Date: Sep. 3, 2020

(65) Prior Publication Data
US 2022/0244178 A1  Aug. 4, 2022

(30) Foreign Application Priority Data
Feb. 28, 2019  (DE) .............. 10 2019 202 739.3

(51) Int. Cl.
*A61B 3/10* (2006.01)
*G01B 9/02002* (2022.01)
(Continued)

(52) U.S. Cl.
CPC ............. *G01N 21/39* (2013.01); *A61B 3/102* (2013.01); *G01B 9/02002* (2013.01);
(Continued)

(58) Field of Classification Search
CPC .. G01N 21/39; G01N 21/45; G01N 2021/399; A61B 3/102; G01B 9/02002; G01B 9/02004; G01B 9/02091
See application file for complete search history.

(56) References Cited

U.S. PATENT DOCUMENTS

| 8,632,181 B2 | 1/2014 | Bublitz et al. |
| 2006/0280216 A1* | 12/2006 | Jayaraman ............. G01N 21/39 372/50.124 |

(Continued)

FOREIGN PATENT DOCUMENTS

| DE | 10 2008 028 312 A1 | 12/2009 |
| WO | WO 2018/119077 A1 | 6/2018 |

OTHER PUBLICATIONS

Bossen, et al, "FPGA-based non-uniform fast Fourier transform (NUFFT) algorithm for real-time OCT signal processing," Proc. SPIE 8571, Optical Coherence Tomography and Coherence Domain Optical Methods in Biomedicine XVII, 85712Y; https://doi.org/10.1117/12.2006391 (Year: 2013).*

(Continued)

*Primary Examiner* — Kara E. Geisel
*Assistant Examiner* — Jonathon Cook
(74) *Attorney, Agent, or Firm* — DeWitt LLP (57) ABSTRACT

A method of controlling a semiconductor-laser-diode-based SS-interferometer system (SS=swept source), for a wide range of application suitable for use in ophthalmology, for example for imaging and for determining biometric measurement values of the eye. In a method according to the invention, by application of periodic current modulation, the operation of single semiconductor laser diode is designed such that a highly coherent spectral laser line can be adjusted with a highest possible repetition rate over a wide wavelength range. The parameters: center wavelength, sweep rate, sweep range, optical power in the eye and coherence (Continued)

length are adjusted such that the method is suitable for imaging and biometric applications via whole-eye scans. A semiconductor-laser-diode-based SS-interferometer system is provided, for biometric measuring of the eye. Embodiments are based for example on optical, coherence tomographic scan images. Applications lie in ophthalmological diagnostics, treatment and the preparation of surgical procedures and follow-up thereof.

19 Claims, 2 Drawing Sheets

(51) Int. Cl.
  *G01B 9/02004* (2022.01)
  *G01B 9/02091* (2022.01)
  *G01N 21/39* (2006.01)
  *G01N 21/45* (2006.01)
(52) U.S. Cl.
  CPC ..... *G01B 9/02004* (2013.01); *G01B 9/02091* (2013.01); *G01N 21/45* (2013.01); *G01N 2021/399* (2013.01)

(56) References Cited

U.S. PATENT DOCUMENTS

| | | | | |
|---|---|---|---|---|
| 2010/0091806 | A1* | 4/2010 | Luo | H01S 5/0683 372/29.011 |
| 2011/0255054 | A1* | 10/2011 | Hacker | G01B 9/0203 356/479 |
| 2013/0120711 | A1* | 5/2013 | Hacker | A61B 5/0066 351/206 |
| 2013/0308097 | A1* | 11/2013 | Ebersbach | A61B 3/102 351/206 |
| 2018/0344149 | A1* | 12/2018 | Chong | A61B 3/0025 |
| 2020/0221068 | A1* | 7/2020 | Schmidt | B60Q 1/04 |

OTHER PUBLICATIONS

Michalzik, R., Ebeling, K.J. (2003). Operating Principles of VCSELs. In: Li, H.E., Iga, K. (eds) Vertical-Cavity Surface-Emitting Laser Devices. Springer Series in Photonics, vol. 6. Springer, Berlin, Heidelberg. https://doi.org/10.1007/978-3-662-05263-1_3 (Year: 2003).*
Li K, Chase C, Qiao P, Chang-Hasnain CJ. Widely tunable 1060-nm VCSEL with high-contrast grating mirror. Opt Express. May 15, 2017;25(10):11844-11854. doi: 10.1364/OE.25.011844. PMID: 28788744. (Year: 2017).*
"Retinal, anterior segment and full eye imaging using ultrahigh speed swept source OCT with vertical-cavity surface emitting lasers" Biomedical Optics Express, vol. 3, No. 11, Nov. 1, 2012 (Nov. 1, 2012), pp. 2733-2751 DOI: 10.1364/BOE.3.002733 ISSN: 2156-7085, XP055133476 (Year: 2012).*
"VCSEL-based swept source for low-cost optical coherence tomography" Biomedical Optics Express, United States, vol. 8, No. 2, Feb. 1, 2017 (Feb. 1, 2017), p. 1110 Doi: 10.1364/BOE.8.001110 ISSN: 2156-7085, XP055702048 (Year: 2017).*
"Improving the Resolution of Retinal OCT with Deep Learning : 22nd Conference, MIUA 2018, Southampton, UK, Jul. 9-11, 2018, Proceedings" In: Communications in computer and information science, DE, : Springer, pp. 325-332, vol. 894, Jan. 1, 2018 (Jan. 1, 2018), ISSN: 1865-0929, XP055703789) (Year: 2018).*

International Search Report for PCT/EP2020/055291, mailed Jul. 8, 2020, 3 pages.
English translation of International Search Report for PCT/EP2020/055291, mailed Jul. 8, 2020, 2 pages.
Written Opinion of the ISA for PCT/EP2020/055291, mailed Jul. 8, 2020, 8 pages.
English translation of Written Opinion of the ISA for PCT/EP2020/055291, mailed Jul. 8, 2020, 7 pages.
Ireneusz Grulkowski et al. "Retinal, anterior segment and full eye imaging using ultrahigh speed swept source OCT with vertical-cavity surface emitting lasers" Biomedical Optics Express, vol. 3, No. 11, Nov. 1, 2012 (Nov. 1, 2012), pp. 2733-2751 DOI: 10.1364/BOE.3.002733 ISSN: 2156-7085, XP055133476.
Sucbei Moon et al. "VCSEL-based swept source for low-cost optical coherence tomography" Biomedical Optics Express, United States, vol. 8, No. 2, Feb. 1, 2017 (Feb. 1, 2017), p. 1110 DOI: 10.1364/BOE.8.001110 ISSN: 2156-7085, XP055702048.
Ying Xu et al. "Improving the Resolution of Retinal OCT with Deep Learning : 22nd Conference, MIUA 2018, Southampton, UK, Jul. 9-11, 2018, Proceedings" In: Communications in computer and information science, DE, : Springer, pp. 325-332, vol. 894, Jan. 1, 2018 (Jan. 1, 2018), ISSN: 1865-0929, XP055703789.
Koici-II Iiyama et al. "High-Resolution FMCW Reflectometry Using a Single-Mode Vertical-Cavity Surface-Emitting Laser" IEEE Photon/CS Technology Letters, IEEE Service Center, Piscataway, NJ, US, vol. 23, No. 11, Jun. 1, 2011 (Jun. 1, 2011), pp. 703-705 DOI: 10.1109/LPT.2011.2131124 ISSN: 1041-1135, XP011480009.
Hefferman Gerald et al. "Extended-bandwidth frequency sweeps of a distributed feedback laser using combined injection current and temperature modulation" Review of Scientific Instruments, AIP, Melville, NY, US, vol. 88, No. 7, Jul. 27, 2017 (Jul. 27, 2017), [retrieved on Jul. 27, 2017] DOI: 10.1063/1.4991817 ISSN: 0034-6748, XP012220422.
B. Potsaid u.a.: MEMS tunable VCSEL light source for ultrahigh speed 60kHz—1 MHz axial scan rate and long range centimeter class OCT imaging. Proc. SPIE 8213, Optical Coherence Tomography and Coherence Domain Optical Methods in Biomedicine XVI, 82130M (Feb. 8, 2012). doi: 10.1117/12.911098.
Cole, Garret D. [u.a.]: Ultra-widely tunable VCSELs. [2021] 44 S. URL: http://www.aoimcro.com/tech/Cole_TUM_27_Sep_2021.pdf [abgerufen am May 20, 2019.
Udo Haberland, Vladimir Blazek, Hans Juergen Schmitt: Chirp optical coherence tomography of layered scattering media. J. Biomed. Opt. 3(3) (Jul. 1, 1998), S. 259-266. doi: 10.1117/1.429889.
V. Jayaraman, u.a.: Recent advances in MEMS-VCSELs for high performance structural and functional SS-OCT imaging. Proc. SPIE 8934, Optical Coherence Tomography and Coherence Domain Optical Methods in Biomedicine XVIII, 893402 (Mar. 4, 2014). doi: 10.1117/12.2041718.
VIXAR Inc.: Operation of VCSELs under pulsed conditions— Increasing VCSEL output power. Plymouth, MN, USA, 2010 S. 1-10—Firmenshcrift. URL: http//www.auniontech.com/ueditor/file/20170921/1505977465336422.pdf [abgerufen am May 20, 2019.
Yano, Tetsuo, u.a.: Wavelength modulation over 500 kHz of micromechanically tunable InP-based VCSELs with Si-MEMS technology. IEEE Journal of Selected Topics in Quantum Electronics, 2009, 15. Jg., Nr. 3, S. 528-534. doi: 10.1109/JSTQE.2009.2015468.
Nanoplus GmbH: DFB laser diodes from 760 nm to 830 nm. Gerbrunn, 2017 (Rev. DFB760.10). 2 S.—Firmenschrift. URL: https://nanoplus.com/fileadmin/user_upload/Data_sheets/nanoplus_DFB_760-830nm.pdf [abgerufen am May 20, 2019].

* cited by examiner

METHOD FOR CONTROLLING A SEMICONDUCTOR-LASER-DIODE-BASED SS-INTERFEROMETER SYSTEM

Examples thereof are changes in length of one of the two superposed light paths for length measurement, changes in refractive index for measuring material properties or minimal changes in the distance between the test masses in gravitational wave detectors.

Accordingly, numerous solutions are known in accordance with the prior art.

One specific interferometric application is optical coherence tomography (OCT), as an imaging method. By application of OCT systems it is possible to obtain 2- and 3-dimensional recordings of scattering materials with micrometer resolution. The main field of use of OCT is medicine, in particular ophthalmology.

In the OCT methods, coherent light is used with the aid of an interferometer for distance measurement and imaging at reflexive and scattering samples. On the human eye, the OCT methods yield measurable signals during the scan into the depth, on account of the changes in refractive index occurring at optical interfaces and on account of volume scattering. Optical coherence tomography is a very sensitive and fast method.

In order to make the acquisition of measurement values even more effective here, OCT systems based on the so-called "swept source" technique (SS-OCT) have been used in recent years. This involves tuning the frequency of the light source and thereby generating the depth signals. This technique makes it possible to carry out whole-eye scans on the human eye. However, this necessitates appropriate selection and control of the illumination source.

Present-day SS-OCT systems use complex microelectromechanical laser diode systems (MEMS) in order to tune spectral laser lines with a high coherence length (in the range of cm to m) with a high repetition rate (in the range of kHz to MHz) over a wide wavelength range of up to 150 nm. This is necessary in order to obtain high-resolution images very rapidly over a high measurement depth particularly in transparent organic tissue, such as the human eye, with a high axial resolution.

In optics, the coherence length is the maximum path length difference or propagation time difference permitted between two light beams from the same source in order that a (spatially and temporally) stable interference pattern still arises when they are superposed.

Of course, detection in OCT systems cannot take place without noise. Consequently, a reflection in the sample can only be detected if it yields a signal that is greater than the noise background in the OCT system.

This smallest still detectable reflection is a very important characteristic variable of OCT systems and is referred to as sensitivity and usually indicated in dB.

When considering sensitivity, the so-called "sensitivity roll-off" criterion should furthermore be taken into account, which is understood to mean the decrease in the amplitude of the interference signal as the difference in length between reference and sample arms increases.

A sensitivity (taking account of the "sensitivity roll-off" criterion) of −6 dB is defined for the OCT systems described here.

In accordance with the known prior art, however, there are also already efforts and attempts to use other laser diodes, for example the VCSEL (Vertical Cavity Surface Emitting Laser). An overview can be found in the article "Ultra-Widely Tunable VCSELs" by Garrett D. Cole in [1].

By way of example, in this respect reference is made to a single-mode (also called mono-mode) VCSEL laser diode from Philips, the technical data of which are described in [3]. This VCSEL laser diode, tunable over 2 nm, can be operated thermoelectrically in a temperature range of 10-40° C. with a slightly different center wavelength in that case.

In [4], Sucbei Moon and Eun Seo Choi describe low-cost OCT systems based on VCSEL laser diodes which are tunable by a current pulse or a thermal shock momentarily at a wavelength of approximately 1300 nm. In order to preclude motion artefacts during the measurement of the eye, very high sweep rates (repetition rate) of the laser in the range of 10-100 kHz are specified, however. The disclosed design for a low-cost OCT system with a wavelength of 1300 nm is unsuitable for a whole-eye measurement, however, owing to absorption in the vitreous body. Furthermore, at the wavelength of 1300 nm used, a sweep range (tuning range) of at least 25 nm (better 75 nm) would have to be realized in order to enable a required resolution in air of 30 µm (better 10 µm). The prospect of attaining such a sweep range is not indicated. The combinations of parameters mentioned here are therefore not very suitable for being able to construct an optical biometer which satisfies the requirements in respect of a competitive system.

DE 10 2008 028 312 A1 describes the use of a VCSEL laser diode for eye measurement. In that case, the laser diode is operated in a spectrally narrowband fashion at a wavelength of approximately 850 nm with a coherence length of typically 100 mm and a spectral width of approximately 0.007 nm and thus offers a sufficient scan depth for the measurement of the entire eye length. In order to be able to achieve the required measurement accuracy given a maximum spectral tuning of 3 nm at a wavelength of 850 nm, a slow tuning of these laser diodes in the range of <10 Hz should be assumed, however. This therefore gives rise here to the need for additional use of a position recognition system, which is required for slowly tuned laser diodes in order to be able to measure moving objects, such as the human eye, with a comparatively slow repetition rate of the tuned laser.

WO 2018/119077 A1 describes a miniaturized, inexpensive OCT system for ophthalmological applications. In particular, the system is provided for measuring the thickness of the retina, wherein the system, owing to its compactness and handiness, is suited to patients being able to perform the measurements themselves at home. The SS-OCT systems described here are based on VCSEL laser diodes controlled by periodic variation of the current. A whole-eye scan is not possible with the systems described on account of the parameters used. Instead, systems are described in which the optical unit includes an optical scanning element in order to enable the light source to be moved to different locations on the retina.

LITERATURE

[1] Cole et. al.; "Ultra-Widely Tunable VCSELs", http://www.aomicro.com/tech/Cole_TUM_27_Sep_2012.pdf
[2] Nanoplus; "DFB laser diodes from 760 nm to 830 nm", https://nanoplus.com/fileadmin/user_upload/Data_sheets/nanoplus_DFB_760-830nm.pdf
[3] Philips, 760/763 nm single-mode VCSEL http://www.photonics.philips.com/pdf/ULM76X-SingleMode_TO5.pdf
[4] Moon et.al.; "VCSEL-based swept source for low-cost optical coherence tomography", Biomedical Optics Express, vol. 8, No. 2, Feb. 1, 2017, p. 1110-1121

[5] Hogan B.; "Operation of VCSELs Under Pulsed Conditions", VIXAR Application Note, 21 Jan. 2010
[6] Bublitz et al, "SS-OCT-Interferometry for measuring a sample; U.S. Pat. No. 8,632,181 B2
[7] Choi W, et al, "Phase-sensitive swept-source optical coherence tomography imaging of the human retina with a vertical cavity surface-emitting laser light source"; Opt Lett. 2013; 38(3): 338-340

SUMMARY OF THE INVENTION

Embodiments of the present invention include a method for controlling a simple semiconductor-laser-diode-based SS-interferometer system which is suitable for imaging and biometric measurements on the eye. In this case, the parameters for controlling the laser beam source are to be optimized to the effect that a wide wavelength range is tunable in conjunction with a high coherence length and a comparatively high repetition rate. In this case, the biometric measurements of the eye are intended to be able to be carried out by application of whole-eye scans, in particular.

Example embodiments of the invention include a method in which, by application of periodic current modulation, the operation of simple semiconductor laser diodes is configured such that a highly coherent spectral laser line is tunable with a highest possible repetition rate and over a wide wavelength range. In this case, the parameters: Center wavelength, sweep rate, sweep range, optical power at the eye and coherence length are adapted such that the method is suitable for imaging and biometric applications by application of whole-eye scans.

A first group of example embodiments relates to the configuration or adaptation of the semiconductor laser diode used, such as, for example, the type of laser diode and surface emitter used, the configuration of the active zone thereof and the optimization of the emission geometry.

A second group of example embodiments relates to the control of the semiconductor laser diodes, in particular the periodic current modulation and/or the setting and stabilization of a defined nm/K gradient, wherein a Peltier element can be used.

In the method for controlling a semiconductor-laser-diode-based SS-interferometer system, wherein, by application of periodic current modulation, the operation of semiconductor laser diodes is configured according to the invention such that a highly coherent spectral laser line is tunable with a high as possible repetition rate and over a wide wavelength range, in particular the following parameters are provided in this case:
  a center wavelength in the range of 600-1400 nm,
  a sweep rate in the range of 100 Hz-100 kHz,
  a sweep range in the range of 3-75 nm and
  an optical power at the eye in the range of 50-20 000 µW, given a coherence length of at least 20 mm.

With regard to the optical power of the semiconductor-laser-diode-based SS-interferometer system, provision is made, with a given wavelength, for providing as far as possible the maximum permissible optical power at the patient's eye in order to be able to realize a maximum signal/noise ratio while complying with the safety regulations. Since approximately 50% of the power of the beam source (semiconductor laser diode) in the optical system of the interferometer should be taken into account as losses, correspondingly higher powers of the semiconductor laser diode are planned:

| center wavelength $\lambda$ | maximum optical power at the eye | power of the semiconductor laser diode |
|---|---|---|
| 600 nm | 390 µW | >0.8 mW |
| 800 nm | 620 µW | >1.2 mW |
| 1050 nm | 1.95 mW | >4 mW |
| 1300 nm | 15.6 mW | >31 mW |

The optical power relates to the radiation power which is permitted to be applied to the human eye, this being defined in the laser standard DIN EN 60825-1, for example. Said power is dependent on the wavelength and the temporal shaping of the laser beam. For the sake of simplicity, the laser powers presented here relate to cw operation of the diode and laser class 1. Other pulse peak values can be employed for pulsed radiation and other laser classes. If appropriate, country-specific standards must also be taken into account.

The proposed semiconductor-laser-diode-based SS-interferometer system is provided in particular for biometric measurements of the eye. Since the presentations are for example based on scan recordings effected by optical coherence tomography, the main application resides in ophthalmological diagnostics, therapy and preparation of surgical interventions and follow-up examination thereof.

BRIEF DESCRIPTION OF THE DRAWINGS

The invention is described in more detail below on the basis of exemplary embodiments. In this respect.

DETAILED DESCRIPTION

The semiconductor-laser-diode-based SS-interferometer system consists of a semiconductor laser diode with a control unit, wherein the control unit is designed to control the operation of the semiconductor laser diode by application of periodic current modulation such that a highly coherent spectral laser line is tunable with a highest possible repetition rate over a wide wavelength range.

To that end, the control unit is designed to vary time and amplitude of the current pulses for the periodic current modulation.

Semiconductor laser diodes used are VCSEL laser diodes, for example, which can be based on a GaAs-wafer surface emitter or a single-mode AlGaInP-wafer with a multi-quantum-well structure.

In particular, the invention provides for using only single-mode VCSEL laser diodes. Multi-mode VCSEL laser diodes are not provided.

Single-mode VCSEL laser diodes are distinguished by a very small instantaneous linewidth, a high coherence length and the measurement depth required for biometric measurements. In this case, the single-mode VCSEL laser diode is intended to have a coherence length of at least 20 mm, but in particular 60 mm. This ensures that even very long eyes, such as occur when there is a high degree of myopia, can be reliably measured.

Consequently, the system is also suitable for mass screening for myopia, such as is currently being carried out in Asia, for example, in order to stem increasing myopia in the population.

The single-mode VCSEL laser diode should be used with a spectral width of the laser line of typically 100 MHz. Corresponding lasers are available from Trumpf, for example.

For the setting and stabilization of a defined nm/K gradient, the VCSEL laser diode can be embedded into an active semiconductor material, wherein the active semiconductor material is appropriately dimensioned and adapted to the adjoining semiconductor material layers. In order to optimize the heat sink produced, thermally conductive material and/or a Peltier element can be used.

In particular, the design of the VCSEL laser diode can be configured such that the active zone thereof is modifiable in order to realize a continuous optical power at the eye of up to 20 mW.

According to the invention, a VCSEL laser diode having a wavelength in the range of 600-1400 nm, for example of approximately 1050 nm, is provided.

It should be taken into account here that a shorter wavelength requires a smaller tuning range (referred to as: sweep range) for the same resolution and the repetition rate, in particular, is the greatest technological challenge in this technology. Accordingly, short wavelengths of 600 nm, for example, in the red spectral range and of 700 nm, for example, in the IR range are best suited to this. By way of example, a single-mode AlGaInP laser diode with a multi-quantum-well structure and a wavelength of 690 nm is suitable. Furthermore, VCSEL laser diodes with a wavelength of 840 nm are available and well suited.

For cataract penetration or higher penetration depth into the tissue, however, VCSEL laser diodes with a wavelength of approximately 1050 nm are better suited and should therefore be preferred.

Furthermore, according to the invention, a VCSEL laser diode with a repetition rate (referred to as: sweep rate) of 100 Hz-100 kHz, for example 1 kHz is provided. In this case, as delimitation with respect to [6] in particular, the SS-interferometer system according to the invention is intended not to require an additional movement signal of the eye in order to be able to evaluate the measurement results.

It should be taken into account here that, for compensation of motion artefacts, a repetition rate of 1 kHz is sufficient and, with a lowest possible repetition rate, it is possible to achieve a signal/noise ratio that is all the higher for a given limited power of the laser diodes. In particular, a repetition rate of 1-3 kHz is provided as an optimum range for biometric eye measurements.

Furthermore, it should be taken into account that there is a dependence of the instantaneous line width, the coherence length and the measurement depth on the tuning rate and the repetition rate of the A-scan.

An optimization of this dependence is provided according to the invention. In this case, primary importance is attached to a sufficient measurement depth of 60 mm for whole-eye biometry.

At least a frequency of 1 kHz is chosen for the tuning rate/repetition rate of the A-scan in order to be able in any case to preclude motion artefacts of the eye. An increase to up to 100 kHz is provided for an embodiment of the biometric measuring system if the measurement depth of 60 mm is not undershot as a result.

A further technical challenge in the selection and control of a suitable VCSEL laser diode can be seen in the temperature gradient of the wavelength change present. A temperature change of 50 K would accordingly be required for a tunability of 5 nm.

In order to realize large tuning ranges with a repetition rate of approximately 1 kHz, commercially available VCSEL laser diodes have to be modified or they should be operated in a pulsed manner. To that end, the control unit present is designed to vary time and amplitude of the current pulses for the periodic current modulation.

For this purpose, the invention provides for the periodic current modulation (electrical tuning) to be effected independently of the direction of the wavelength change, such that both up-sweep and down-sweep are used.

In particular, provision is made, when tuning the wavelength with the aid of the current pulse, to use both the up-sweep and the down-sweep of the wavelength for application in the simple swept-source VCSEL biometry according to the invention. In this case, a longer wavelength is set as the current rises. Consequently, during the down-sweep it should be taken into consideration that the wavelength will shorten in this current pulse interval.

It is generally known that a temperature gradient of approximately 0.1 nm/K can be realized. A temperature change of 50 K would thus be required for a tunability of 5 nm.

The invention provides for increasing this gradient to >0.1 nm/K, for example to approximately 0.3 to 0.5 nm/K.

That is achieved by selecting an appropriate active semiconductor material. However, it is also possible for the VCSEL laser diode additionally to be embedded into an active semiconductor material.

VCSEL laser diodes for wavelengths of between 600 nm and 1400 nm are based on GaAs-wafers for example as surface emitters.

Furthermore, provision is made for using single-mode AlGaInP laser diodes with a multi-quantum-well structure given a wavelength of 690 nm and a large temperature gradient of at least 0.25 nm/K.

In order to optimize the heat sink in order to realize a high temperature gradient within the possible operating temperature of the VCSEL laser diode (e.g. −20 to +70° C.), provision is made for example for coupling material having a high thermal conductivity, such as copper, indium, or the like, to the semiconductor material.

Besides the wavelength tuning of the single-mode VCSEL laser diodes that is caused purely electrically according to the invention, in addition a combination of the purely electric with an additional thermal tuning of the wavelength is also provided.

To that end, the electrically controlled module is operated in a manner synchronized with the heat sink, which tunes the ambient temperature of the single-mode VCSEL laser diode of, in principle, −80° C. to +180° C. in a certain range of e.g. 100 K with a highest possible repetition rate of >100 Hz, for example >1 kHz. The sweep range (tuning range of the wavelength in nm) can thus be extended and the resolution of the biometer can thus be increased.

Active cooling with the aid of a Peltier element can additionally be effected.

However, since additional cooling can result in condensation water condensing on the exit window of the VCSEL laser diode, the invention provides for providing the exit window of the VCSEL laser diode with heating.

As already mentioned, for cataract penetration or higher penetration depth into the tissue, VCSEL laser diodes with a wavelength of approximately 1050 nm are better suited.

According to the invention, an optical power at the eye in the range of 200 µW to a maximum of 2000 µW, for example of greater than 1000 µW (given a wavelength of 1050 nm), is provided in this case.

It should be taken into account here that a higher optical power is permitted to be realized only within the scope of the laser safety regulations. Achieving higher optical powers necessitates changes in the design of the VCSEL laser diodes. For this purpose, it is possible, for example, to vary the active zone or other parameters of the VCSEL laser diodes in order to realize an optical power of up to 2 mW.

For the construction of a VCSEL-based SS-interferometer system, the invention provides for the laser radiation emitted by the semiconductor laser diode to be coupled into the interferometer by use of free-space or fiber optics. To that end, it is necessary for the design of the VCSEL laser diode to be configured accordingly. In both cases the beam quality for given power is an important criterion since it defines the laser power that can be used for carrying out the measurement.

Particularly in the case of a fiber-based design, importance should be attached to carrying out input coupling as far as possible without any losses. In the case of monomode fibers having a fiber diameter of 5 µm, it is possible to achieve virtually lossless input coupling with losses of <10% given a numerical aperture NA=0.14. Input coupling in monomode fibers having a core diameter of 3 to 9 µm is generally provided.

A further example embodiment of the invention relates to the generation of a wavelength-controlled current pulse. By evaluating the currents of two photodiodes having different spectral behaviors, a measurement signal of the wavelength can be generated and used as a feedback system in a simple manner using analog electronics.

That is described by way of example below for the wavelength range around 1050 nm. In this wavelength range, the change in spectral sensitivity is only approximately +0.1 A/W per 100 nm in the case of InGaAs photodiodes and approximately −0.5 A/W per 100 nm in the case of Si photodiodes. Fluctuations of the power from the laser have the same effect on both photodiodes, however. Therefore, after suitable normalization of the current of the Si photodiode with the current of the InGaAs photodiode, all that remains is a dependence of the resulting current on the wavelength which is approximately 0.4 A per 100 nm (4 µA/nm). This measurement signal can then be used to shape the current pulse so as to achieve the desired profile of the wavelength change.

A profile of the wavelength over time which corresponds to an equidistant change in the wavenumber over time would, for example be produced. The spectral information in the interference signal (frequency domain) could thus be transformed without further equalization directly by Fourier transformation to the measurement result in the space domain.

Suitable shaping of the current pulses can be effected by the wavelength-dependent signal being digitized and processed algorithmically (improvement e.g. by filtering and averaging). The current pulse is then iteratively deformed until the desired result is achieved.

Besides suitable shaping of the current pulses until attainment of linearity or an equidistant change in the wavenumber over time, the invention furthermore provides for using structured current pulses in which the current is interrupted a number of times, that is to say that a rapidly clocked current fills the envelope of a current pulse. This clocked current pulse is optimized according to the invention until its structure in terms of spacing of the individual pulses and amplitude of the individual pulses results in an equidistant change in the wavenumber of the single-mode VCSEL laser diode over time.

A further possibility would be a closed analog or digital control loop with a desired wavelength profile as setpoint value, the wavelength-dependent signal as measurement value and the current pulse as actuating signal.

The invention furthermore provides for optimizing the shaping of current pulses with a continuous change of the current within a pulse so that a widest possible sweep range (tuning range of the wavelength in nm) of the single-mode VCSEL laser diode is produced. In this regard, ranges of >3 nm or for example >8 nm up to 20 nm are provided.

Besides the suitable shaping of the current pulses until attainment of a widest possible sweep range (tuning range of the wavelength in nm), the invention furthermore provides for using structured current pulses in which the current is interrupted a number of times, that is to say that a rapidly clocked current fills the envelope of a current pulse. This clocked current pulse is optimized according to the invention until its structure in terms of spacing of the individual pulses and amplitude of the individual pulses results in a maximum sweep range up to approximately 20 nm (tuning range of the wavelength in nm) of the single-mode VCSEL laser diode over time.

In a final embodiment of the invention, the short current pulse is chosen in a range above the threshold current $I_{th}$, with a duration of the current rising edge of <500 µs, for example <50 µs down to ≈1 µs. Thus, in addition to the thermally induced spectral sweep range described, which is e.g. 0.1 nm/K, a non-thermally induced extension of the spectral sweep range (athermal spectral sweep range) is achieved. The effect used according to the invention is based on the purely electrically induced shift of the electronic levels/band gap of the semiconductor laser material on account of the high electric field strengths applied momentarily. This extended portion of the spectral sweep range is produced in particular by way of the type of current pulse and the rising edges thereof. One thing that is advantageous about this operating mode is the low or negligible outlay with regard to the thermal stability of the SS-OCT system. Cooling and thermal stabilization can be minimized or avoided in this operating mode.

This operating mode according to the invention is set if the condition $$\Delta\lambda > \Delta T \Delta\lambda_{therm}$$

holds true, wherein $\Delta\lambda$—corresponds to the spectral sweep range, $\Delta\lambda_{therm}$—corresponds to the thermally induced spectral sweep range (in nm/K) and $\Delta T$—corresponds to the temperature change during the current pulse (in K).

This operating mode can be effected metrologically e.g. with an integrated temperature sensor for $\Delta T$ at the laser chip and a measurement during the current pulse in combination with the measurement of the spectral sweep range $\Delta\lambda$ achieved in conjunction with known spectral drift behavior of the laser material $\Delta\lambda_{therm}$ measured in the steady state.

In the proposed method for controlling a semiconductor-laser-diode-based SS-interferometer system, the operation of the semiconductor laser diodes, by application of periodic current modulation, is configured such that a highly coherent spectral laser line is tunable with a highest possible repetition rate and over a wide wavelength range. According to the invention, the following parameters are provided in this case:

a center wavelength in the range of 600-1400 nm,
a sweep rate in the range of 100 Hz-100 kHz,
a sweep range in the range of 3-75 nm and
an optical power at the eye in the range of 50-20 000 µW, given a coherence length of at least 20 mm.

Figure 1:
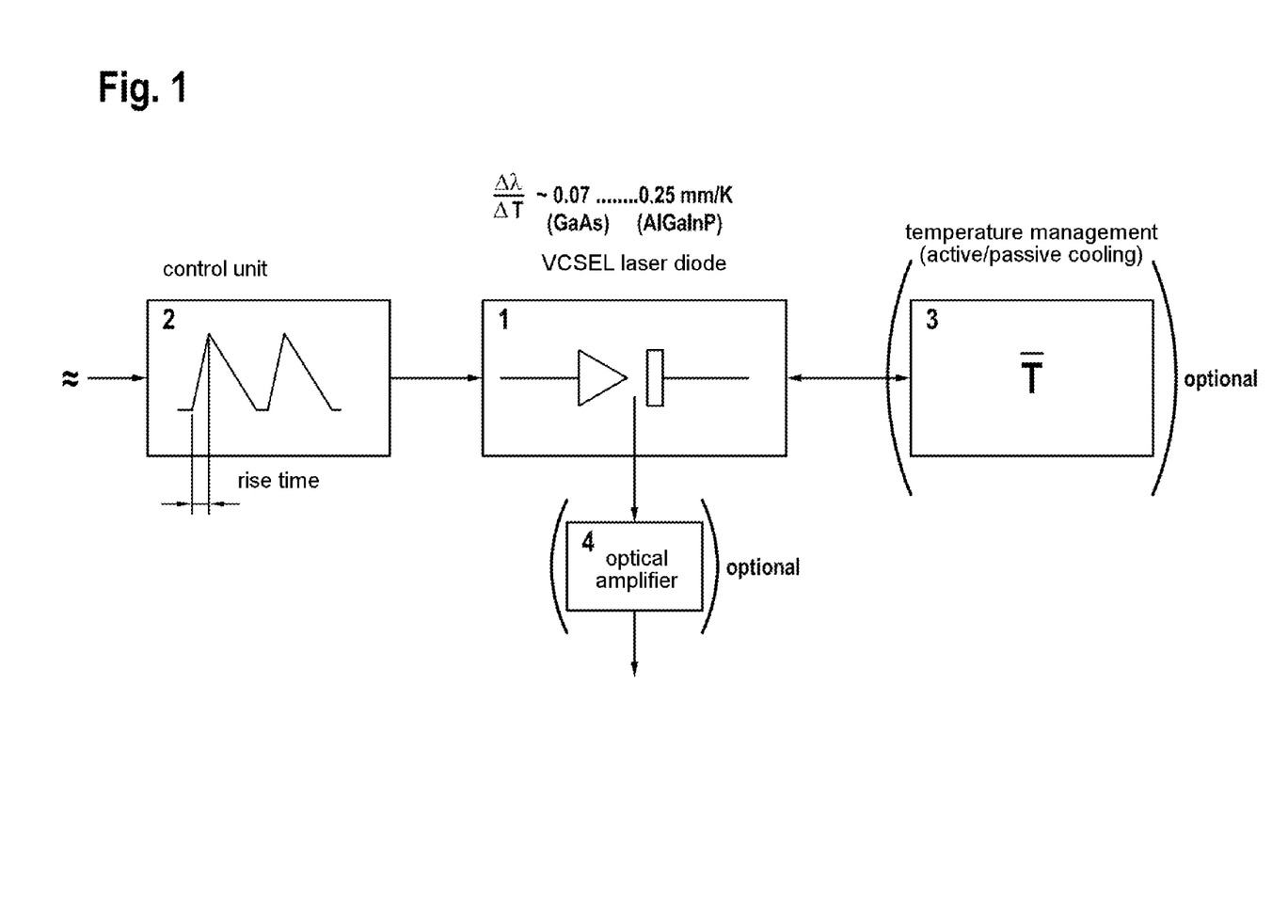
FIG. 1: depicts a basic illustration concerning the control of a semiconductor-laser-diode-based SS-interferometer system according to the invention by application of periodic current modulation.

In this respect, FIG. 1 shows a basic illustration of the control of a semiconductor-laser-diode-based SS-interferometer system according to the invention by application of periodic current modulation.

The semiconductor-laser-diode-based SS-interferometer system consists of a semiconductor laser diode 1 with a control unit 2, wherein the control unit 2 is designed to control the operation of the semiconductor laser diode 1 by application of periodic current modulation such that a highly coherent spectral laser line is tunable with a highest possible repetition rate over a wide wavelength range.

To that end, the control unit 2 is designed to vary time and amplitude of the current pulses for the periodic current modulation. In particular, the control unit 2 is designed to output short rise times of the current pulses for electrically pumping the semiconductor diode 1.

In this case, the semiconductor laser diode 1 is, in particular, a VCSEL laser diode with a variation of the wavelength of the highly coherent spectral laser line depending on the present operating temperature. In this regard, for example, a variation $\Delta\lambda_{therm}/\Delta T$ of 0.07 nm/K is provided for a GaAs-based semiconductor laser diode and a variation of 0.25 nm/K is provided for an AlGaInP-based semiconductor laser diode.

It should additionally be noted that, according to the invention, owing to the short rise time of the current pulses from the control unit 2, it is possible to achieve a wider tuning range of the wavelength $\Delta\lambda$ beyond the value known as a result of the thermal variation ($\Delta\lambda > \Delta T \Delta\lambda_{therm}$)

Optionally, primarily for stable long-term operation of the SS-laser source, provision is made of temperature stabilization or temperature management by use of a heat sink 3, which can operate actively and also passively. If the heat capacity of the semiconductor laser diode 1 and its heat sink already present are sufficient for stable operation, these additional features of the heat sink 3 can also be dispensed with.

In order to optimize this heat sink 3, thermally conductive material and/or a Peltier element can be used. Active cooling of the laser chip of the semiconductor laser diode 1 is provided synchronously with the periodic current modulation by the control unit 2 only in the times outside the current rising edge (rise time).

Besides the function of the cooling of the laser chip owing to the heating by the current pulse of the control unit 2 for thermally stable operation, the heat sink 3 is optionally also provided for additional heating of the laser chip of the semiconductor laser diode 1 synchronized with the current pulse of the control unit 2 only within the current rising edge. As a result, it is possible to increase the thermally induced wavelength detuning by way of an increase in the temperature change $\Delta T$ not only on the basis of the electrically induced temperature increase, but additionally also on the basis of this optional direct active temperature increase within the time of the current rising edge.

The semiconductor laser diode 1, for example outputs an output power in the range of a few mW with the desired parameters of an SS-interferometer system for OCT and biometric applications, which power can compensate for losses in the further optical system and achieves a good signal/noise ratio while taking into consideration the maximum ophthalmologically usable intensities in the diagnostic applications. If the output power of the semiconductor laser diode 1 is too low, a semiconductor-based optical amplifier (referred to as: Semiconductor Optical Amplifier, for short: SOA) SOA 4 is optionally integrated into the optical beam path.

Figure 2:
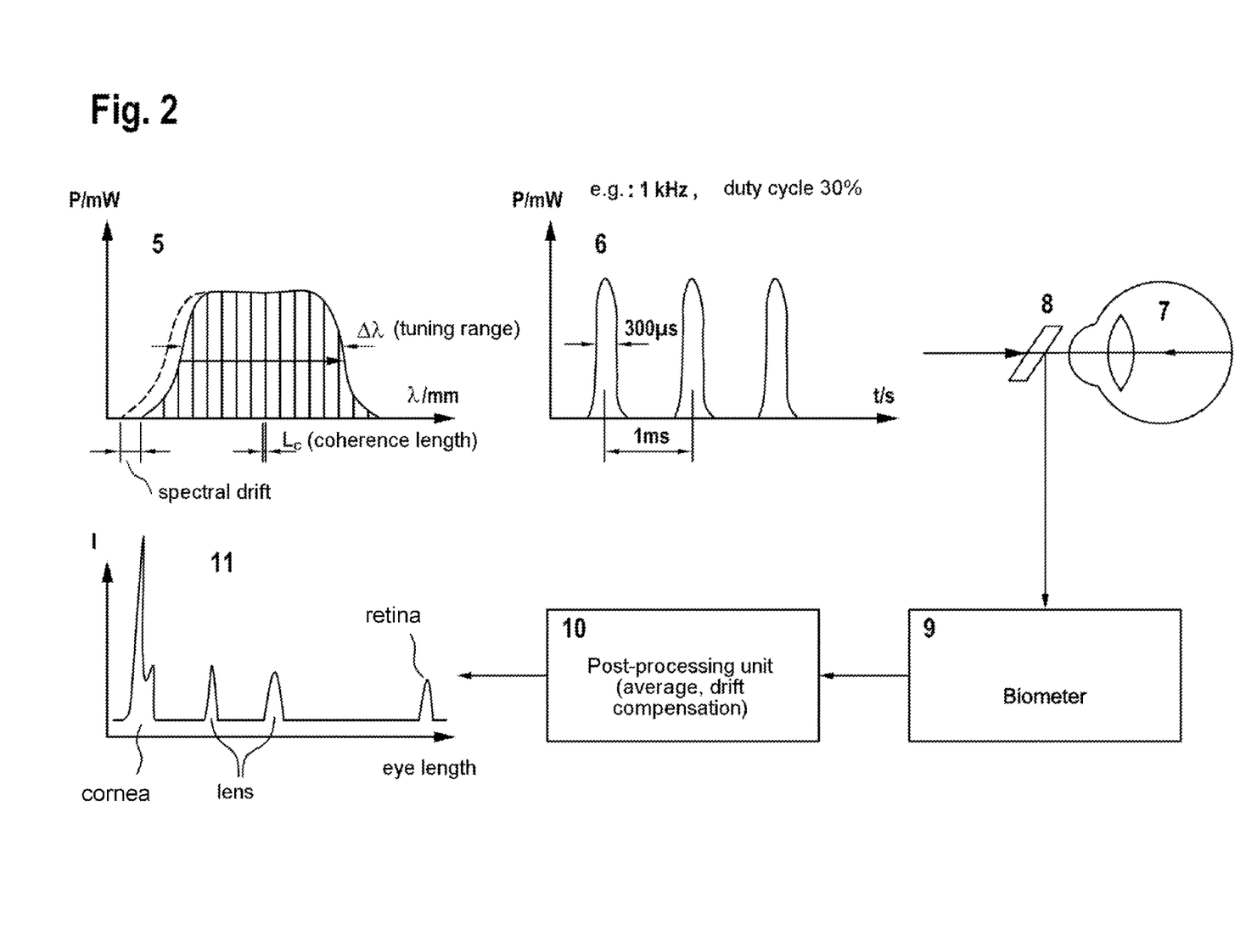
FIG. 2: depicts some further optical parameters of the radiation emitted by the semiconductor-laser-diode of the SS-interferometer system.

FIG. 2 illustrates some further optical parameters of the radiation emitted by the semiconductor laser diode of the SS-interferometer system.

The diagram 5 schematically depicts the tuning of the individual highly coherent wavelengths over a wavelength range $\Delta\lambda$, the so-called sweep range, with a power P in the mW range. The spectral resolution of the sweep determines the coherence length Lc or the measurement depth in air, as indicated in the graph. This functionality is realized within a current rising edge (rise time) of the semiconductor laser diode 1 according to the invention. This illustration shows a shift (spectral jitter) of the tuning range $\Delta\lambda$, which can arise in particular as a result of heating of the semiconductor laser diode 1 after relatively long operation. This effect can be suppressed by temperature management by use of the heat sink 3.

The diagram 6 schematically depicts, using an example, the temporal emission parameters with individual laser pulses, in which each laser pulse of 300 µs contains the spectral tuning characteristic of the highly coherent wavelength within $\Delta\lambda$ according to diagram 5. These laser pulses are shown here with a repetition rate of 1 kHz and thus a pulse spacing of 1 ms. A duty cycle of 30% is realized in this case. In this regard, after an active current pulse of 300 µs, for example, the laser chip has a time of 700 µs again for thermal and/or electromagnetic relaxation for functionality with long-term stability.

The laser radiation of the semiconductor laser diode 1 with the properties according to the diagrams 5 and 6 is coupled into the eye 7 to be examined within an interferometric system (not illustrated in detail). The light intensity backscattered from the eye is detected by use of a beam splitter 8 within a biometer 9. The broad signals of the biometer 9 are processed with the aid of a post-processing unit 10 in order to output a depth scan over the entire eye 7 (also called A-scan), in particular with information concerning the position and the distances of the cornea, the lens and the retina as measurement result 11. In a procedure that is not depicted schematically here, said A-scan can be scanned laterally over the pupil opening of the eye in order to produce a sectional image of the aforementioned distances in the eye 7 as a so-called B-scan.

In order to compensate for the undesired drift—which arises as a result of thermal ambient influences and changes in the operating temperature—of the tuning range of the wavelength (sweep range) that is to say the so-called spectral jitter, the single-mode VCSEL laser diode can be installed on a temperature-regulated heat sink in the temperature range of, in principle, −80° to +180° C. with stabilized temperature with a temperature stability of approximately +/−1 K. In this case, moreover, at low temperatures as a result of high currents it is also possible to achieve high output powers of the monomode VCSEL laser diode.

In order to realize the wavelength drift depending on the temperature without an additional heat sink, the invention provides for using a fiber-optic Bragg grating in the interferometer of the short-coherent biometric measuring system, which predefines a wavelength reference with which the measuring system can be continuously recalibrated.

An (e.g. fiber-based) Bragg reflector/grating (FBG) can be used for better spectral stabilization of the tuning range. Said reflector is introduced in this system in such a way that during a tuning process a light reflection arises given an exactly defined wavenumber. Said light reflection can be recorded jointly with the interference signal. It serves as a reference for accurate and absolute spectral localization of the spectral interference signal.

In this respect, W. Choi et al. describe, in [7], a solution in which one of the detection arms leads to the balanced detector via an FBG. In the detection signal, the FBG results in a "notch" that can be used for the spectral referencing of the signals.

A first variant of the method relates to the imaging on the basis of an SS-OCT system. Here, too, a highly coherent spectral laser line is intended to be tunable with a highest possible repetition rate and over a wide wavelength range.

In this variant of the proposed method, the following embodiments are possible, for example.

According to a first embodiment, one, a plurality or all of the following example parameters are provided:
a center wavelength of 1050 nm,
a sweep rate of 1 kHz,
a sweep range of 16 nm and
an optical power at the eye of a maximum of 2 mW, given a coherence length of greater than 60 mm.

According to a second embodiment, one, a plurality or all of the following example parameters are provided:
a center wavelength of 840 nm,
a sweep rate of at least 1 kHz,
a sweep range of at least 9 nm and
an optical power at the eye of a maximum of 0.8 mW, given a coherence length of greater than 60 mm.

According to a third configuration, one, a plurality or all of the following example parameters are provided:
a center wavelength of 600 nm,
a sweep rate of at least 1 kHz,
a sweep range of 5 nm and
an optical power at the eye of a maximum of 0.4 mW, given a coherence length of greater than 60 mm.

By way of example, a measurement depth in air or coherence length Lc of approximately 25 mm would be sufficient for the measurement of the front section of the eye as far as the back side of the lens.

With a measuring arrangement for determining the biometric values, measurement values such as eye length AL, lens thickness LD, anterior chamber depth VKT and the cornea thickness HHD, for example for the purpose of the IOL calculation, are determined substantially from so-called A-scans or B-scans. An axial resolution of approximately 100 µm in air is sufficient for this purpose.

By way of example, for this purpose, reference is made to the IOLMaster 500 from Zeiss Meditec AG, in which a multimode laser diode with a full width at half maximum of $\Delta\lambda \sim 2.7$ nm with a center wavelength of 785 nm realizes a resolution of 100 µm in air.

The axial resolution $\Delta z$ for a Gaussian power spectral density is defined as:

$$\Delta z = \frac{2\ln 2}{\pi} * \frac{\lambda^2}{\Delta\lambda}$$

in which: $\Delta\lambda$ defines the full width at half maximum and $\lambda$ defines the center wavelength.

Other typical power spectral densities can also be approximated well by the above formula. In the case of a semiconductor laser diode with a center wavelength of 1050 nm, a $\Delta\lambda \approx 5$ nm is necessary in order to realize the resolution of 100 µm in air.

If a semiconductor laser diode with a central wavelength at 840 nm and an electrical tuning range of 5 nm is used, an even better value of a resolution of approximately 65 µm in air is obtained. At this wavelength of 840 nm, the axial resolution of 100 µm in air that is required for biometry is already achieved with a tuning range of approximately 3 nm.

Accordingly, this gives rise to the following values:

| center wavelength $\lambda$ | full width at half maximum $\Delta\lambda$ | resolution in air $\Delta z$ |
|---|---|---|
| 600 nm | 16 nm | 10 µm |
| 600 nm | 5 nm | 30 µm |
| 600 nm | 3.5 nm | 50 µm |
| 800 nm | 28 nm | 10 µm |
| 800 nm | 10 nm | 30 µm |
| 800 nm | 6 nm | 50 µm |
| 1050 nm | 50 nm | 10 µm |
| 1050 nm | 16 nm | 30 µm |
| 1050 nm | 10 µm | 50 µm |
| 1300 nm | 75 nm | 10 µm |
| 1300 nm | 25 nm | 30 µm |
| 1300 nm | 15 µm | 50 µm |

The invention provides a full width at half maximum (which corresponds to the sweep range of the semiconductor laser diodes) in the range of 10-100 nm, for example of at least 16 nm at 1050 nm.

Furthermore, a VCSEL laser diode with a repetition rate (referred to as: sweep rate) of 100 Hz-100 kHz, for example ≥1 kHz, is provided according to the invention.

In this context, reference is made once again to the already mentioned relationship between motion artefacts, repetition rate and signal/noise ratio.

The sensitivity of the SS-OCT system scales with the energy deposited in the tissue (number of photons) and not with the peak power. Therefore, the invention strives to choose the sweep rate to be fast enough to preclude motion artefacts of the eye, but also long enough to be able to make available a sufficiently high pulse energy for a given power of the laser diode.

In this case, an optical power in the range of 200 µW to a maximum of 20 000 µW, for example a maximum of 2000 µW (at a wavelength of 1050 nm), is provided according to the invention.

Here, too, reference is made once again to complying with the laser safety regulations already mentioned.

However, it is also possible to vary other parameters. In this regard, for example, the line width of the VCSEL laser diode can be widened.

The invention furthermore provides a coherence length Lc of at least 60 mm, since the measurement depth resulting therefrom is necessary for measuring the entire human eye.

However, an SS-OCT system with low axial resolution of >30 µm, for example >50 µm, can also be realized. This is of interest for example for the tomographic and volumetric representation of the entire eye (anterior chamber to the fundus of the eye). The loss in axial resolution can likewise be compensated for by "machine-learning" algorithms. For this purpose, it is necessary first to record images with standard resolution, and to use these images for training the algorithms. The machine-learning-based algorithms then learn to improve the resolution even in the images with low axial resolution.

In order to extend the field of application of the technology according to the invention, provision is made, in particular, of an improved evaluation of the whole-eye scans as A-scan and/or as B-scan with the aid of algorithms based on machine learning/deep learning/artificial intelligence. In this case, an advantage of the biometer according to the invention is the high measurement depth, allowing whole-eye scans with a high repetition rate of e.g. 28 kHz A-scan rate. What is disadvantageous, however, is that the resolution on account of the small sweep range of approximately 5 nm is low in comparison with modern high-resolution ss-OCT systems having a sweep range of up to 100 nm. Therefore, provision is made for measuring completely and/or partly at least a number of approximately 20 eyes of patients both using the biometer according to the invention and at the same time using some other commercially available ultra-high-resolution OCT system. By application of algorithms based on machine learning/deep learning/artificial intelligence, the known high-resolution measurements are then intended to be compared with the measurements of the biometer according to the invention and be assessed. As a result, these algorithms are intended to improve later individual measurements of the biometer in the A- and/or B-scan in terms of their resolution and accuracy.

A second variant of the method for controlling a semiconductor-laser-diode-based SS-interferometer system relates to biometric applications, in particular by application of whole-eye scans.

In the proposed method for controlling a semiconductor-laser-diode-based SS-interferometer system, by application of periodic current modulation, the operation of semiconductor laser diodes is configured such that a highly coherent spectral laser line is tunable with a highest possible repetition rate and over a wide wavelength range. According to the invention, the following parameters are provided for biometric applications in this case:
  a center wavelength in the range of 600-1400 nm,
  a sweep rate in the range of 100 Hz-100 kHz,
  a sweep range in the range of 3-20 nm and
  an optical power at the eye in the range of 50-20 000 µW, given a coherence length of at least 20 mm.

According to one example embodiment, one, a plurality or all of the following example parameters are provided for whole-eye scans:
  a center wavelength of 1050 nm,
  a sweep rate of 1 kHz,
  a sweep range of 5 nm and
  an optical power at the eye of a maximum of 2 mW, given a coherence length of greater than 60 mm.

The semiconductor laser diodes are operated by application of periodic current modulation by duration and amplitude and shape (rising edge) of the current pulses being varied.

For a maximum repetition rate it is necessary to achieve a maximum temperature gradient by application of a current pulse within the active VCSEL semiconductor layer. In order, however, in the case of a virtually continuous mode of operation, to be able to achieve a high repetition rate with constant laser parameters, an identical average temperature of the active material has to be ensured.

That is accomplished with just passive cooling of the VCSEL laser diodes according to the invention by application of:

a short current pulse in a range above the threshold current $I_{th}$, wherein in particular the duration of the current rising edge is <500 µs down to ≈50 ns and
  a duty cycle which is sufficient to allow cooling of the active VCSEL semiconductor layer to a stable operating temperature in the range of +/−2 K. In particular, for this purpose, a duty cycle of <50% down to 1%, for example 30%, is provided according to the invention. In this regard, for example, given a current pulse of 100 ns, after 10 000 ns or 10 µs a next current pulse can be effected and a repetition rate of 100 kHz can be set.

According to one example embodiment, a VCSEL-based SS-interferometer system according to the invention can be characterized by the following technical parameters:
  a sweep rate of 28 kHz,
  a duty cycle of 30%
  at an average laser wavelength of 840 nm
  a sweep range of 5 nm
  an output power of the VCSEL laser diode of 2 mW which corresponds to a power at the eye of 0.2 mW and thus a measurement sensitivity of 100 dB.

In particular, in the case of this optimization, it is provided that a higher peak power can be achieved if a shorter driver current pulse is used, such that a duty cycle of <10% can be realized. However, the energy (number of photons) deposited in the tissue can also become lower by a factor of >10.

The invention provides a full width at half maximum (which corresponds to the sweep range of the semiconductor laser diodes) in the range of 3-20 nm, for example of approximately 5 nm at 1050 nm for biometric application.

According to the invention, a duty cycle, adapted with regard to the measurement sensitivity and the thermal stability, in the range up to 1% to 50%, for example of 30%, is furthermore realized in order to achieve a stable steady-state operating temperature of the VCSEL-based tuning SS-interferometer system.

Since a minimum repetition rate of 1 kHz is provided according to the invention, with current pulses having a duration of 100 ns even a duty ratio of 0.01% would be possible, which means a cooling time 10 000 times longer than the current pulse time in the active laser material. In order to keep the complexity for the required control within limits, a duty cycle of 0.1% is realistic. It is thereby possible to establish a stable steady-state operating temperature of the SS-OCT system. Within the scope of the limitations of the pulse energy required for the measurement that have already been described above, a duty cycle of 10% is striven for and a first practical solution has been found with a duty cycle of 30%. Since even with a duty cycle of 30% the spectral tuning range remains permanently stable and no spectral drift takes place, the configuration chosen according to the invention has ensured good heat dissipation for the active volume of the laser diode.

In the example embodiment mentioned above, it was possible to ensure an average power of the diode emission of 2 mW. In the context of the application of this tunable VCSEL laser diode, the VCSEL-based SS-interferometer system makes it possible to provide a measurement power at the eye of 200 µW and to achieve a biometric measurement of the eye with a sensitivity of 100 dB.

The invention furthermore provides for controlling the current pulse for pumping the laser source temporally in terms of its profile amplitude in such a way that a profile of the emitted wavelengths that is linear over the time of the current pulse is obtained within the spectral tuning range of the laser emission. This is advantageous, for example, in order to minimize error sources in the evaluation of the measurement signals.

As already mentioned, the sensitivity of the VCSEL-based SS-interferometer system scales with the energy (number of photons) deposited in the tissue and not with the peak power. Therefore, the invention provides an advantageous optimization in which during pulsed operation the laser diode allows a >10-fold power, which in principle is still regarded as feasible in practice.

Ultimately, the thermal loading restricts the output power of the laser diode. Therefore, an optimum tuning range is provided in particular at low operating temperatures.

Accordingly, for the operation of the VCSEL-based SS-interferometer system according to the invention, provision is made for defining and setting a stable nm/K gradient for the VCSEL laser diode.

As already mentioned, a temperature gradient of approximately 0.1 nm/K can be realized and a temperature change of 50 K is thus required for a tuning range of 5 nm. The invention provides for setting said gradient to >0.1 nm/K, for example to approximately 0.3 to 0.5 nm/K. This can be achieved inter alia by the measures mentioned above.

In this case, an optical power in the range of 200 µW to a maximum of 20 000 µW, for example a maximum of 2000 µW (at a wavelength of 1050 nm), is provided according to the invention.

Therefore, the invention provides for tuning the driver current of the laser diode in a range above the threshold current $I_{th}$, the minimum and the maximum current value of said range resulting in an output power of the laser diode for the measurement at the eye in the corneal plane of at least 50 µW.

According to a further example embodiment, clock fluctuations of <1 ns, a repeatability of the current pulses of <10 ns and an amplitude stability of <+/−5% are to be set and ensured for the periodic current modulation.

Therefore, for optimizing the already discussed repeatability of the tuning range, provision is made for:
  setting a very small clock fluctuation for the control pulses in the range of <1 ns,
  keeping the repeatability of the control pulses in their sequence at <10 ns, and
  setting their amplitude stability in the temporal profile at <+/−5%.

This ensures that the tuning wavelength range remains constant. A change in the wavelength range of >0.1 nm would influence both the axial resolution and the axial scaling and thus the accuracy of the biometric measurements.

Furthermore, particularly in the case of inadequate compliance with the abovementioned necessary stability requirements in respect of the spectral tuning range, provision is made for correcting the variation of the trigger and driver signals by application of a mechanically stable reference signal of the interferometer. The correction can be effected for example by correlation and registration of the spectral interference patterns of the reference signal.

The solution according to the invention for constructing a simple tunable diode laser is based on the fact that a wavelength change is achievable when there is a temperature change in the active laser material. In this case, said temperature change can be effected indirectly by the electric current pulse or/and by additional heating or cooling.

In addition to this effect desired according to the invention, however, the temperature change in the active material of the laser diode is also accompanied by a change in the output power for a given pump current. Therefore, firstly, the invention provides for choosing a design for the laser diode in which the change in the output power depending on the operating temperature is small or reproducible. Furthermore, with regard to this dependence, an optimization of the operating conditions mentioned above is provided.

Besides the technical challenges already mentioned, however, it is necessary to take account of even further dependencies that influence the choice and control of suitable VCSEL laser diodes.

The application of the measurement technique according to the invention to the moving eye requires fast measurement times in order to be able to preclude motion artefacts in the measurement signal. The measurement times should be approximately </=1 ms for an individual measurement. Accordingly, a combination of duty cycle and sweep rate of 10% and 100 Hz, for example, should be chosen. Given this temporal tuning rate, the spectral tuning width in the range of 3-20 nm is then likewise necessary in order to ensure the required resolution. The known behavior of laser diodes, however, is that particularly in the case of slow tuning rates a high tuning width is obtained and thus a further challenge for the realization of the measuring system according to the invention. The choice of an optimum version on the basis of the design of the laser diodes is provided for this combined requirement.

Furthermore, a spectral tuning width that is constant in absolute terms is required in order to be able to evaluate the measurement signals in a reproducible manner. On the other hand, on account of the repeated electrical/thermal tuning of the laser diode that is required during the envisaged measurement operation, the consequence is a temperature drift and thus a wavelength drift of the tuning range.

The choice of an optimum version of a laser diode having e.g. a high thermal conductivity or a high heat capacity and thus a small undesired temperature drift is provided for this requirement.

A large sweep range necessitates the setting of a high temperature of a VCSEL laser diode. At high temperatures, however, there is a decrease in the optical power of the laser diode.

Furthermore, the abovementioned dynamic thermal behavior of the VCSEL laser diodes is dependent on the operating temperature per se. In this regard, the following are obtained at a higher operating temperature:
  a higher laser threshold and
  a lower maximum power $P_{max}$ and a lower maximum current $I_{max}$ Consequently, the invention provides for choosing an operating temperature </=room temperature of approximately 20° C., for example <10° C., or for cooling the laser diode to its minimum permitted operating temperature.

The solution according to the invention provides an SS-interferometer system which is based on a VCSEL laser diode and is suitable for use in ophthalmology, in particular for determination of biometric measurement values of the eye.

The present SS-OCT system is tunable over a wide wavelength range, with a high coherence length and a comparatively high repetition rate, and is thus suitable for biometric measurements of the eye in particular by application of whole-eye scans.

The solution according to the invention for constructing a simple tunable diode laser is based on the fact that a wavelength change is achievable when there is a temperature change in the active laser material. In this case, said temperature change can be effected indirectly by the electric current pulse or/and by additional heating or cooling.

As described above, a temperature gradient of approximately 0.1 nm/K can be realized and a temperature change of 50 K is thus required for a tuning range of 5 nm. The invention provides for setting said gradient to >0.1 nm/K, for example to approximately 0.3 to 0.5 nm/K. This can be optimized inter alia by the described choice of the active semiconductor laser material, the choice of suitable operating parameters and the thermal management of the system.

The invention claimed is:

1. A method for controlling a simple semiconductor-laser-diode-based swept-source (SS)-interferometer system suitable for whole eye scans, comprising:
    applying periodic current modulation to configure operation of semiconductor laser diodes by combined thermal tuning and electrical tuning such that a highly coherent spectral laser line is tuneable with a high as possible repetition rate and over a wide wavelength range; and
    utilizing the following parameters:
        a center wavelength in a range of 600-1300 nm,
        a sweep rate in a range of 100 Hz-100 kHz,
        a sweep range in a range of 3-75 nm and
        an optical power at an eye in a range of 50-20 000 µW,
        given a coherence length of at least 20 mm;
        current pulses with a duration of 1 µs at a repetition rate of 100 kHz or with a duration of 10 µs at a repetition rate of 10 kHz by which the periodic current modulation is applied.

2. The method as claimed in claim 1, further comprising utilizing at least one of the following parameters for imaging by application of an OCT system:
    a center wavelength of 1050 nm,
    a sweep rate of at least 1 kHz,
    a sweep range of at least 16 nm and
    an optical power at the eye of a maximum of 2 mW,
    given a coherence length of greater than 60 mm.

3. The method as claimed in claim 1, further comprising utilizing at least one of the following parameters for imaging by application of an OCT system:
    a center wavelength of 840 nm,
    a sweep rate of at least 1 kHz,
    a sweep range of at least 9 nm and
    an optical power at the eye of a maximum of 0.8 mW,
    given a coherence length of greater than 60 mm.

4. The method as claimed in claim 1, further comprising utilizing at least one of the following parameters for imaging by application of an OCT system:
    a center wavelength of 600 nm,
    a sweep rate of at least 1 kHz,
    a sweep range of at least 5 nm and
    an optical power at the eye of a maximum of 0.4 mW,
    given a coherence length of greater than 60 mm.

5. The method as claimed in claim 1, further comprising utilizing a low axial resolution of >30 µm for the imaging by application of an OCT system.

6. The method as claimed in claim 5, further comprising compensating for loss in resolution by application of image processing algorithms.

7. The method as claimed in claim 1, further comprising effecting the periodic current modulation independently of the direction of the wavelength change, such that both up-sweep and down-sweep are used.

8. The method as claimed in claim 5, further comprising utilizing at least one of the following parameters for whole-eye scans:
    a center wavelength of 1050 nm,
    a sweep rate of at least 1 kHz,
    a sweep range of at least 5 nm and
    an optical power at the eye of a maximum of 2 mW,
    given a coherence length of greater than 60 mm.

9. The method as claimed in claim 1, further comprising additionally modulating an electronic band gap (of an electronic level) of the semiconductor laser material by application of high electric field strengths applied momentarily, for which it holds true that:

$$\Delta\lambda > \Delta T \Delta\lambda_{therm}$$

wherein $\Delta\lambda$—corresponds to the spectral sweep range,
$\Delta\lambda_{therm}$—corresponds to the thermally induced spectral sweep range (in nm/K) and
$\Delta T$—corresponds to the temperature change during the current pulse (in K).

10. The method as claimed in claim 1, further comprising utilizing a sweep rate of 28 kHz, a duty cycle of 30%, given an average laser wavelength of 840 nm and a sweep range of 5 nm, thereby achieving a continuous output power of the semiconductor laser diode of 2 mW and a continuous power at the eye of 0.2 mW, which corresponds to a measurement sensitivity of 100 dB.

11. A method for controlling a simple semiconductor-laser-diode-based swept-source (SS)-interferometer system suitable for whole eye scans, comprising:
    applying periodic current modulation to configure operation of semiconductor laser diodes by combined thermal tuning and electrical tuning such that a highly coherent spectral laser line is tuneable with a high as possible repetition rate and over a wide wavelength range; and
    utilizing the following parameters for biometric applications on an eye:
        a center wavelength in the range of 600-1300 nm,
        a sweep rate in the range of 100 Hz-100 kHz,
        a sweep range in the range of 3-20 nm and
        an optical power at the eye in the range of 50-20 000 µW,
        given a coherence length of at least 20 mm,
        current pulses with a duration of 1 µs at a repetition rate of 100 kHz or with a duration of 10 µs at a repetition rate of 10 kHz by which the periodic current modulation is applied.

12. The method as claimed in claim 11, further comprising effecting the periodic current modulation independently of the direction of the wavelength change, such that both up-sweep and down-sweep are used.

13. The method as claimed in claim 11, further comprising making an amplitude of the current pulses in a range above threshold current $I_{th}$.

14. The method as claimed in claim 11, further comprising making the duration of a rising edge of the current pulses in a range of <500 µs to 50 ns.

15. The method as claimed in claim 11, further comprising making clock fluctuations <1 ns, a repeatability of the current pulses of <10 ns and an amplitude stability of <+/−5% for the periodic current modulation.

16. The method as claimed in claim 11, further comprising controlling a current pulse by application of a feedback system on a basis of knowledge of instantaneous wavelength, as a result of which a known change in a wavenumber over time is realized.

17. The method as claimed in claim 11, further comprising effecting a linear change in a wavenumber over time.

18. The method as claimed in claim 11, further comprising effecting a linear change in a wavenumber over time.

19. The method as claimed in claim 11, further comprising making a feedback system include two different photosensitive materials.

* * * * *